United States Patent [19]

Gagin

[11] Patent Number: 4,639,219
[45] Date of Patent: Jan. 27, 1987

[54] SURGICAL BALL HOOKS

[75] Inventor: William P. Gagin, Sheboygan, Wis.

[73] Assignee: American Orthodontics Corporation, Sheboygan, Wis.

[21] Appl. No.: 351,278

[22] Filed: Feb. 22, 1982

[51] Int. Cl.⁴ .............................................. A61C 7/00
[52] U.S. Cl. .................................................. 433/22
[58] Field of Search ................................... 433/22, 19

[56] References Cited

U.S. PATENT DOCUMENTS 3,158,934 1/1964 Waldman ............................. 433/19

FOREIGN PATENT DOCUMENTS 335395 2/1936 Italy ...................................... 433/19

OTHER PUBLICATIONS

Rocky Mountain Catalogue 40, 1973, p. 33.
American Orthodontics Catalog VII, 1980, pp. 102, 103.

Primary Examiner—Robert Peshock
Attorney, Agent, or Firm—Lloyd L. Zickert

[57] ABSTRACT

Surgical ball hooks for intermaxillary fixation that are adjustably positionable on an archwire and which include a tubular base received by the archwire and an elongated bar or arm fixed at one end to the base and at right angles to the base and having its other end ball shaped. The tubular base may be seamless or split wherein the seamless version is mounted on the wire prior to placement of the wire and the split version may be mounted onto the wire subsequent to placement.

3 Claims, 7 Drawing Figures

SURGICAL BALL HOOKS

This invention relates in general to a dental appliance to be used for intermaxillary fixation of the upper and lower jaws, and more particularly to a surgical hook appliance that may be easily mounted onto an archwire prior to or subsequent to placement of the archwire for intermaxillary fixing the jaws subsequent to surgical repair or resection, and still more particularly to a surgical ball hook appliance for intermaxillary fixation.

Correction of dental facial deformities are most often corrected through a combination of surgical and orthodontic treatment. Such deformities may be congenital or caused by an accident. In either case, treatment usually requires fixing the maxilla and mandible together for a period of time until healing is partially or completely achieved. This is generally accomplished by mounting orthodontic appliances on the teeth, placement of an archwire on the appliances, and interconnecting the archwire and/or the appliances of the upper and lower jaws to obtain intermaxillary fixation with the teeth directly in occlusion or occluding on a splint.

Heretofore, the appliances mounted on the teeth generally include brackets which are fixed to bands that are in turn cemented to the teeth. However, it may be possible in certain cases to effectively mount the brackets onto the teeth by a direct bonding procedure. Preferably, the brackets are of the edgewise type having an edgewise or rectangular archwire receiving slot and, accordingly, receive an edgewise or rectangular archwire that is appropriately secured to the brackets. Following the placement of the wires, it is then common to use ligature wires connected between the archwires and/or the brackets. Threading ligature wires around the archwires and/or the bracket is time-consuming and difficult to achieve. Moreover, applying wire between brackets of the upper and lower arches requires those brackets to take the entire force of the interconnection which sometimes causes failure of the connection of the bracket with a tooth, thereby impairing the integrity of the connection between the jaws.

Heretofore, they have also soldered or welded wire spurs to the archwires prior to archwire placement. This procedure required considerable laboratory time and caused delay in completing the fixation process. Further, the spurs were not movable once fastened to the archwire, and in some cases where they might not be in the proper place, it was necessary to remove the archwire and reposition the spurs. Moreover, many times the archwire would become annealed or softened in the welding or soldering procedures which impaired the structural integrity of the connection of the spur to the wire as well as the rigidity of the wire. Moreover, inasmuch as the ends of the spurs are relatively sharp, they are discomforting to patients, and during the fixation process the surgeon's glove quite often snagged on the spurs and become damaged which would cause delay in the process.

Another known method of fixation involved bending loops in the archwire prior to placement, which loop could then be used for ligature anchorage. Because relatively heavy wire is needed for fixation, loop bending is difficult and many times the loop interferred with the brackets.

The present invention overcomes the difficulties heretofore encountered during intermaxillary fixation in that the surgical ball hook appliance of the invention considerably reduces the laboratory time needed to prepare the archwires, as the hook of the invention may be slidably placed on the archwire prior to placement or, in another version where a split tube is employed, affixed to the archwire subsequent to placement. Indeed, no laboratory time is needed as the surgeon can easily apply the surgical ball hook of the invention to the archwire as needed.

The appliance of the present invention includes a tubular base which may be seamless or presized or formed so that it can slidably fit directly onto the archwire prior to placement or split so that it can be fitted onto the archwire subsequent to placement, and an elongated bar or arm suitably secured at one end to the tubular base and at right angles to the base and provided with a ball-shaped free end which is comfortable to the patient and avoids the existence of any sharp points which a surgeon's glove might snag or during the fixation process.

The invention eliminates the need to subject the archwire to heat for mounting the appliance on the archwire, thereby eliminating any injury to the structural integrity of the archwire. The appliance further provides an easy target for the surgeon to loop ligature wire over opposing or near opposing appliances on the upper and lower jaws since they are large enough, readily accessible and easily adjustable along the archwire. Moreover, the appliance may be easily positioned so that the hook portion is on the labiobuccal or lingual side of the archwire depending upon the gingiva thickness so as to provide a more efficient connection between upper and lower jaws, while at the same time preventing interference with the gingiva. Looping and tying ligature wire around opposed surgical hooks on the upper and lower jaws dissipates the forces through the archwire between two or three brackets, thereby reducing the possibility of a bracket from breaking the connection to a tooth. By virtue of the appliances being easily adjustable on the archwire, slight vector forces may be established during intermaxillary fixation where such is deemed desirable. When the fixation wires are removed, the same surgical hooks of the invention may also be used to anchor rubber bands which continues a fixation that allows the patient to freely open and close the mouth for eating purposes.

It is therefore an object of the present invention to provide a new and improved appliance for intermaxillary fixation of the upper and lower jaws which materially reduces the laboratory time and surgeon's time for preparing and placement of surgical archwire and the fixation of the upper and lower jaws.

Another object of the present invention is in the provision of a surgical ball hook appliance for intermaxillary fixation which eliminates sharp points, thereby increasing patient comfort and eliminating possible snags of surgeons' gloves during the fixation process.

A still further object of the present invention is in the provision of a surgical ball hook appliance for intermaxillary fixation which is easily adjustable on the archwire and may be mounted on the archwire prior to or subsequent to placement.

Another object of the present invention is in the provision of a surgical ball hook appliance for intermaxillary fixation which may be mounted on a surgical archwire without damaging the wire integrity and which also may be reused.

A further object of the present invention is in the provision of a surgical ball hook appliance for intermaxillary fixation which dissipates the fixation forces between a ligature wire and a plurality of brackets, thereby essentially eliminating possible failure of a bracket attachment to a tooth.

Other objects, features and advantages of the invention will be apparent from the following detailed disclosure, taken in conjunction with the accompanying sheets of drawings, wherein like reference numerals refer to like parts, in which.

Figure 1:
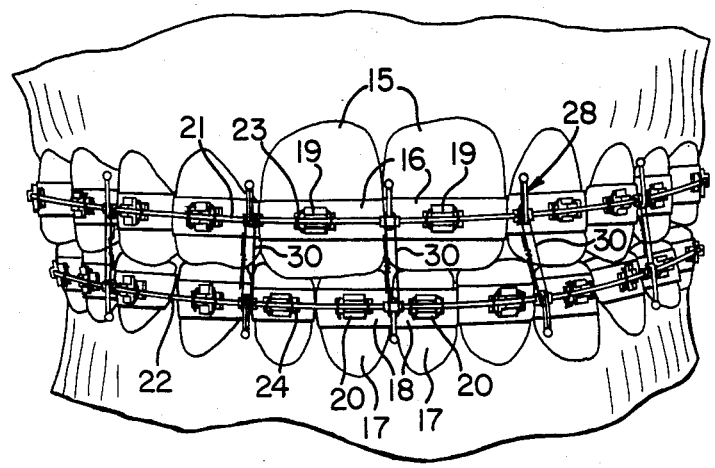
FIG. 1 is a front elevational view of the upper and lower arches having brackets mounted on the teeth, archwires placed in the brackets and the appliance of the invention mounted on the archwires together with the ligature wires connected to the appliances to provide intermaxillary fixation.

Referring now to the drawing and particularly to FIG. 1, the upper and lower jaws of a person are illustrated in closed position where the teeth of the upper and lower arches are in desired occlusion with bracket appliances mounted on the teeth, the surgical ball hook appliances of the invention are mounted on archwires which are secured to the bracket appliances, and ligature wires are looped over the surgical hooks for obtaining intermaxillary fixation. The brackets are affixed to bands which are in turn suitably cemented to the teeth.

Each of the teeth 15 on the upper jaw has a band 16 suitably cemented thereto. Similarly, each of the teeth 17 on the lower jaw has a band 18 cemented thereto. Brackets 19 are suitably affixed to the bands 16 on the upper teeth, while brackets 20 are suitably affixed to the bands 18 on the lower teeth. It will be appreciated that it is well known to use edgewise brackets and archwires for handling intermaxillary fixation so that desired control can be established between the archwires and the brackets. Thus, the brackets 19 and 20 are of the usual edgewise configuration wherein they include a mesiodistally extending rectangular slot for receiving a rectangular archwire in snug relation. An upper rectangular archwire 21 is therefore received in the archwire slots of the brackets on the upper teeth, while a lower archwire 22 is received in the slots of the brackets 20 on the lower teeth. Suitable means is provided for securing the archwires in place on each of the brackets. While elastics may be employed, it is preferred that ligature wires are used in order to firmly afix the archwire against possible movement relative to the brackets. Accordingly, ligature wires 23 are provided on the upper brackets, while ligature wires 24 are provided on the lower brackets.

Figure 2:
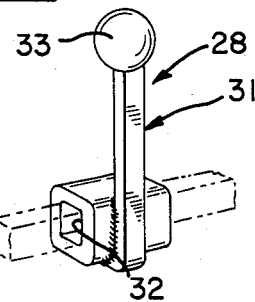
FIG. 2 is an enlarged perspective view of the surgical ball hook appliance of the present invention.
Figure 3:
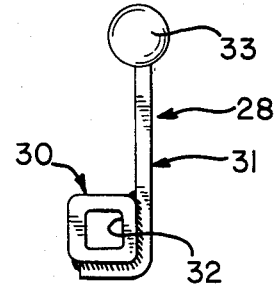
FIG. 3 is a side elevational view of the hook in FIG. 2.
Figure 4:
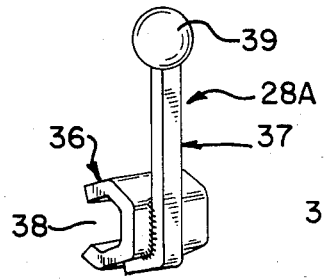
FIG. 4 is a perspective view of the surgical ball hook appliance of the invention where the tube is split.

The surgical ball hook appliance of the present invention, and generally indicated by the numeral 28, is either mounted on the archwires prior to placement or subsequent to placement. In most instances, the appliances will be mounted on the archwires prior to placement of the archwires in the slots of the brackets. In this instance, the appliance with the seamless tube, as shown in FIGS. 2 and 3, would be employed. Where it is necessary to mount an appliance of the invention onto the archwire subsequent to placement in the brackets, the split tube version of the appliance of the present invention, shown in FIGS. 4 to 7, is employed. For purposes of distinguishing between these two types, the seamless tube version will be identified by the numeral 28, while the split tube version will be identified by the numeral 28A.

Once the surgical ball hook appliances are in place, ligature wires may easily be looped around opposing or substantially opposing appliances and the ends of the wires suitably twisted together as shown by the ligature wires 30 in FIG. 1 to complete the intermaxillary fixation of the jaws. It may therefore be readily appreciated that the procedure for achieving intermaxillary fixation would be to first mount the bands having brackets suitably secured thereto onto the teeth and cementing them to the teeth, mounting the desired number of surgical ball hook appliances onto the archwires, placing the archwires in position on the brackets and securing the archwires to the brackets, and thereafter with the surgical ball hook appliances in the desired locations, looping and tying ligature wire over opposed appliances, as shown in FIG. 1. Thereafter, to release the fixation, it is only necessary to remove the ligature wires although if some resilient fixation is desired thereafter, rubber bands may be utilized to interconnect the appliances.

The seamless tube version of the surgical ball hook appliance of the present invention, designated by the numeral 28, includes generally a seamless tube 30 and an elongated bar or arm 31 secured to the tube and at right angles thereto. The tube 30 is provided with a rectangular opening 32 sized to be compatible with the archwire on which it is to be used. This opening extends mesiodistally when the appliance is mounted on the archwire. While it is shown to be square in cross section, it may be shaped to have two opposing sides longer than the other two sides. The word rectangular herein is intended to include not only a square in cross section tube but also one which would have a cross section with a longer dimension in one direction than the other. Most commonly for surgical cases a surgical archwire is 0.021×0.025 inches. Accordingly, the opening for a tube would need to be sufficiently large to permit easy sliding of the tube onto that archwire. The length of the tube 30 is such that it may easily fit between brackets on closely adjacent teeth such as illustrated at the lower anteriors in FIG. 1.

The elongated bar or arm 31 is preferably rectangular in cross section. While the cross section may be square, it is preferable that the width along the tube be greater than the depth. The bar 31 is mounted in a center position on the tube 30 and is wrapped around two sides of the tube, as seen most clearly in FIG. 3, so that it can be firmly attached to the tube. While it may be suitably attached in any fashion, one manner of doing so would be to tack weld the bar to the tube and then solder it in place where the solder would extend completely along the edges of the bar as well as across the free end and at the point where the bar extends upwardly from the tube so that the best possible attachment of the bar is accomplished with respect to the tube.

It is significant that the free end of the bar 31 is ball shaped so that the balled end 33 provides a smooth end that will be comfortable with the patient and at the same time eliminate any sharp points. This is particularly helpful to the surgeon so that the surgeon does not snag his gloves on any sharp points which could cause a delay in the surgical process of fixation. Further, the balled end 33 is of a size that is substantially larger than the cross section of the bar 31. Thus the diameter of the ball-shaped end extends outwardly of all sides of the bar in the mesiodistal, labiobuccal and lingual directions.

Figure 6:
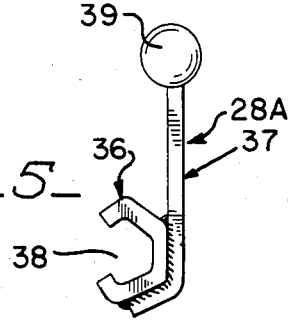
FIG. 6 is a perspective view of the appliance of FIG. 4 mounted on an archwire where the split tube has been closed on the archwire.
Figure 5:
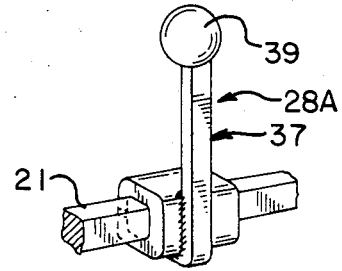
FIG. 5 is a side elevational view of the appliance shown in FIG. 4.
Figure 7:
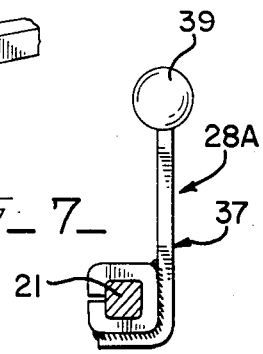
FIG. 7 is a side elevational view of the appliance of FIG. 4 and mounted on the archwire.

As already mentioned, the split tube version of FIGS. 4 to 7 is useful for mounting on an archwire that has already been secured in place to the brackets. This version, designated as 28A, includes a split tube 36 and an elongated bar or arm 37 that is suitably mounted to the split tube in a similar fashion to the seamless tube version of FIGS. 2 and 3. As illustrated particularly in FIGS. 4 and 5, the split tube 36 is provided in its open position so that a mesiodistal slot or opening 38 is defined which is large enough to allow the archwire to move into the tube, after which the tube can be closed, such as illustrated in FIGS. 6 and 7, to provide the mounting of the surgical hook appliance onto the archwire. Closing of the tube may be such as to still allow adjustment of the appliance along the archwire, or it may be closed and crimped so that the appliance will remain in a given position. Similarly, the seamless tube version 28 may be crimped to the archwire to hold it in position if desired. It will be appreciated that the seamless tube version 28A likewise has the upper end of the bar 37 ball shaped at 39 and that the mounting of the bar onto the seamless tube may similarly be accomplished by first tack welding and then soldering. It should be appreciated that the appliance will stay in place along the wire even when the tube is not crimped to the wire following the connection of the ligature wire between opposed appliances as the force generated will hold the appliances in place.

Another important feature of the appliance of the invention, whether it be the seamless tube version 28 or the split tube version 28A, is that the appliance may be mounted on the archwire so that the hook portion or bar 31 will be disposed on the labiobuccal or the lingual side of the archwire. An illustration of mounting the bar on the lingual side is shown in FIG. 1 at the anterior of the arches. The other appliances are mounted so that the bar is on the labiobuccal side. It will be appreciated that the bar or hook may be on the lingual side toward the gingiva in the anterior where it will not interfere with the gum or gingiva, while it must be on the buccal side in the molar region where the gums are closer to the archwire so that the hook portion does not engage the gum.

It will be understood that modifications and variations may be effected without departing from the scope of the novel concepts of the present invention, but it is understood that this application is to be limited only by the scope of the appended claims.

The invention is hereby claimed as follows:

1. An intermaxillary fixation appliance system for securing the jaws of a patient together with the teeth in proper occlusion comprising, edgewise brackets mounted on the upper and lower teeth, said brackets having horizontally rectangular archwire slots, rectangular archwire secured in said slots, a plurality of surgical ball hook appliances mounted on said archwires in opposed relation, each ball hook appliance including a tubular rectangular in cross section base having a rectangular opening therethrough for slidable movement on said archwire to any position between adjacent teeth and brackets, the mating relation between the opening and the archwire preventing rotation therebetween, said base having a length such that it can easily fit between brackets mounted on closely adjacent teeth, an elongated rectangular bar disposed perpendicular to said opening and along adjacent side and bottom walls of said base and extending gingivally of said base to coact therewith and define a hook, means securing the bar to said base, said base being mountable on said archwire so that the bar may be disposed on the labiobuccal or lingual side wall of said base, and a ball-shaped member at the end of said bar having a diameter greater than the maximum cross sectional dimension of the bar, and ligatures extending over said opposed ball hook appliances to fix the jaws together.

2. The surgical ball hook appliance of claim 1, wherein said tubular base is seamless and mountable on the archwire prior to placement of the archwire in the mouth.

3. The surgical ball hook appliance of claim 1, wherein said tubular base is split and mountable on said archwire subsequent to placement in the mouth.

* * * * *